United States Patent [19]

Gendrich et al.

[11] 4,005,063
[45] Jan. 25, 1977

[54] [DES-GLY][10]-GNRH NONAPEPTIDE ANIDE ANALOGS IN POSITION 6 HAVING OVULATION-INDUCING ACTIVITY

[75] Inventors: Ronald Lee Gendrich, Waukegan; Riemond Henry Rippel, Gurnee; John Hunter Seely, Lake Bluff, all of Ill.

[73] Assignee: Abbott Laboratories, North Chicago, Ill.

[22] Filed: May 15, 1975

[21] Appl. No.: 577,815

Related U.S. Application Data

[62] Division of Ser. No. 405,334, Oct. 11, 1973, Pat. No. 3,914,412.

[52] U.S. Cl. .................................... 260/112.5 LH
[51] Int. Cl.$^2$ ................. C07C 103/52; C08H 1/00
[58] Field of Search ......................... 260/112.5 LH

[56] References Cited

UNITED STATES PATENTS 3,914,412  10/1975  Gendrich et al. ........ 260/112.5 LH

OTHER PUBLICATIONS

Fujino et al., Biochem. Biophys. Res. Comm., 57, 1248–1256 (1974).
Martinez et al., Biochem. Biophys. Res. Comm., 59, 1226–1232 (1974).

*Primary Examiner*—Lewis Gotts
*Assistant Examiner*—Reginald J. Suyat
*Attorney, Agent, or Firm*—Paul D. Burgauer; Robert L. Niblack

[57] ABSTRACT

An unnatural nonapeptide with improved biological activities surpassing those of the natural follicle-stimulating luteinizing hormone-releasing hormone (Gn—RH) is described. The new peptide induces ovulation in warm-blooded animals at an oral dose of 5–100 μg./kg.

1 Claim, No Drawings

[DES-GLY]¹⁰-GNRH NONAPEPTIDE AMIDE ANALOGS IN POSITION 6 HAVING OVULATION-INDUCING ACTIVITY

This is a division of application Ser. No. 405,334, filed 10-11-73, now U.S. Pat. No. 3,914,412.

DETAILED DESCRIPTION OF THE INVENTION

Gn—RH which consists of the sequence of pGlu—His—Trp—Ser—Tyr—Gly—Leu—Arg—Pro—Gly—NH₂ in which all the optically active aminoacids are in the L-configuration, has been known for several years. It has found utility particularly in animal husbandry where it has been used to induce ovulation. The method and systems used have been described in Proc. Soc. Exper. Biol. and Med. 143, 55 (1973) by Rippel, et al. Unfortunately, this natural hormone has the disadvantage of having very little oral activity.

It is therefore an object of the present invention to provide a peptide with oral activity. It is another object of this invention to provide a synthetic peptide which shows superior hormonal activity over natural occurring peptides. It is a further object of this invention to provide a synthetic peptide that can be readily assembled from easily accessible aminoacids.

These and other objects are accomplished by providing a compound of the formula:

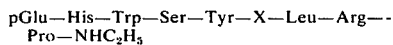

wherein all aminoacids are in the L-configuration with the exception of X, which represents an aminoacid in the D-configuration and having the formula:

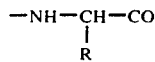

in which R represents a hydrocarbon chain of between 1 and 4 carbon atoms in linear or branched configuration.

In a general embodiment, the compounds of the above formula can easily be made by using the method described by Merrifield in J. Am. Chem. Soc., 85, 2149 (1963). More particularly, N-blocked proline is esterified to a chloromethylated divinylbenzene-styrene copolymer. After deblocking, $N^\gamma$-blocked arginine carrying a labile protective group on the imino-N is coupled to the now free imino group of the proline ester and after deblocking, this sequence of coupling and deblocking steps are repeated with other aminoacids in the sequence of the formula shown under formula I. All of the aminoacids are used in their L-form except for the aminoacid identified as X in said formula.

After all of these aminoacids are linked in the above sequence with the arginine, tyrosine, serine and optionally the histidine carrying protective groups, the nonapeptide is removed from the resin support in known fashion; the polyprotected peptide is then transesterified/ammonolyzed whereby the resin link is replaced by the ethylamide terminal. Subsequent treatment in known fashion removes all the protective groups mentioned above, producing the compound of the structure shown in formula I in substantially pure form and acceptable yield.

The simplest member of the class represented by X in formula I is alanine or the compound wherein R represents the methyl group. Other aminoacids that can take the place of X are the leucine, isoleucine, valine and the unnatural α-aminobutyric acid. The nonapeptide of this sequence show a resemblance to the aminoacid sequence in Gn—RH but distinguishes therefrom in several major respects: Gn—RH is a decapeptide, ending with an unsubstituted amido group while in the above nonapeptide, the terminal glycinamide group of Gn—RH is replaced by the ethylamide group which is directly linked to the now terminal proline. An even more striking difference over Gn—RH is the use of a dextro-acid in the center of the aminoacid sequence. With this change, it was totally unexpected that the new aminoacid chain had biological activity in general; it was even more surprising to find that the biological activity of this compound containing a D-aminoacid had biological activity similar to Gn-RH but at a much higher and much improved level, particularly in view of the fact that most of the biologically active peptides uncovered in recent years are composed of aminoacids exclusively in the L-configuration.

The compounds of formula I act much in the same way as shown in the article referred to above by Rippel, et al; however, the compounds of the present invention induce ovulation in warm-blooded animals at intravenous, intramuscular or subcutaneous single doses of between 0.02 and 1.0 μg./kg. and with a single oral dose of between 2 and 100μg./kg. More specifically, a single injection to a proestrus rat at a level of 0.05 to 0.3 μg./kg. or an oral dose of 30 μg./kg. produces almost certain ovulation. This effect can be easily and beneficially employed in animal husbandry.

In order to show the preparation and use of the compounds of the present invention, reference is made to the following examples which, however, are not intended to limit the invention in any respect.

EXAMPLE 1

Proline carrying as a blocking group the t-butyloxycarbonyl substituent (elsewhere herein referred to as Boc-) on the amino group is esterified by combining it with a chloromethylated divinylbenzene-styrene copolymer (marketed by Schwarz-Mann as Merrifield resin) containing 2% of cross linking, using the method described by Stewart, et al. in "SOLID PHASE PEPTIDE SYNTHESIS", (published in 1969 by Freeman & Company), San Francisco, (page 1). In this manner, a resin is produced which by hydrolysis and aminoacid analysis shows to contain 0.47 millimoles of proline/g. of resin. In an automatic synthesizer developed according to the previously cited Merrifield apparatus, 4.6 g. of this resin/aminoacid material is used for the synthesis of the desired nonapeptide. Each N-blocked aminoacid is added in a three-fold access and allowed to couple to the existing aminoacid-resin ester in the usual coupling cycle. The coupling reaction is carried out for 4.5 hours with continuous shaking and the reaction is subsequently washed six times with methanol-chloroform 1:2 for 1.5 minutes each and 4 times with ethanol for 1.5 minutes each. In each instance, a total volume of 48 milliliters is used and the drain time after shaking usually is about 1.5 minutes.

After coupling, the mixture is washed four times for 1.5 minutes each with dioxane, twice with 4 N hydrochloric acid/dioxane for 5 minutes and 25 minutes, respectively, five times with dioxane for 1.5 minutes each, three times with ethanol for 1.5 minutes each, three times with chloroform for 1.5 minutes each, three times with 10% triethylamine/chloroform for 1.5 minutes each, four times with chloroform for 1.5 minutes each and six times with dichloromethane for 1.5 minutes each. Ordinarily the solvent used for the coupling reaction is dichloromethane or, when the solubility of the blocked aminoacid is low, a mixture of dichloromethane and dimethylformamide. Coupling is effected by the addition of a solution of dicyclohexylcarbodiimide in dichloromethane at a 2.9 fold excess.

The sequence used for deprotection, neutralization and coupling of the next aminoacid is done in a fully automatic system as described above. In this manner, the peptide is assembled using in turn Boc-Arg(Tos), Boc-Leu, Boc-D-Leu, Boc-Tyr(CL$_2$Bzl), Boc-Ser(Bzl), Boc-Trp, Boc-His(DNP), and pGlu wherein all aminoacids are in the L-form except in the leucine so designated.

The resin is removed from the vessel and suspended in 200 ml. of 5% triethylamine/methanol and 100 ml. of distilled ethylamine is added thereto. After 24 hours, the resin is removed by filtration and the solution evaporated to yield a solid. The solid is taken up in glacial acetic acid and applied to a 3 × 50 cm. column of silica gel equilibrated with 5% methanol/chloroform.

The column is eluted with 5 % methanol in chloroform until all traces of N-ethyl dinitroaniline, the yellow by-product of the histidine protecting group DNP is removed. The eluant is then changed to 33% methanol/chloroform and fractions of about 30 ml. each are collected. The compound is located by thin-layer chromatography of aliquots of the fractions (Silica gel G. 33% MeOH/CHCl$_3$, Cl$_2$/tolidine spray). The fractions containing the product are pooled and evaporated to give a solid which is precipitated from methanol with ether. This triprotected nonapeptide (protective groups at Ser, Tyr and Arg) is thus obtained in an amount of 1.69 g., representing an overall yield of 43% of theory.

A 250 mg. sample of the above is placed in a hydrogen fluoride reaction vessel with 250 mg. of anisole and about 5 ml. of anhydrous hydrogen fluoride is distilled into it. After 1 hour at 0° C., the hydrogen fluoride is removed with a stream of dry nitrogen and the residue is taken up in 1% acetic acid. This solution is extracted with ether, and the aqueous phase applied to a 1 × 30 cm. column of a highly basic ion exchange resin marketed by Bio-Rad as AGl × 2 resin) in the acetate form. The product is eluted with 0.1 N acetic acid and localized using thin-layer chromatography (CHCl$_3$/MeOH/32% HOAc: 120/90/40, silica gel G. Cl$_2$/tolidine). The product bearing solution is lyophilized, rechromatographed on a Sephadex G-25 (marketed by Pharmacia of Uppsala, Sweden) column. The product eluted is collected and lyophilized to yield a fluffy white solid $[\alpha]_D^{25} = -31.7°$ (c = 1, 1% HOAc) in a 25% overall yield. An aminoacid analysis shows the expected ratio of all desired aminoacids assembled in the above fashion.

When in the above synthesis, the Boc-D-leucine is replaced by the correspondingly protected α-aminobutyric acid, alanine, isoleucine or valine, the above synthesis proceeds in the same fashion, again in all instances, using the automatic synthesizer described above.

EXAMPLE 2

The nonapeptide made in the previous example and having the structure of formula I wherein X is the D-leucyl link, was dissolved in physiological saline for injection into a group of mature, female rats weighing an average of 200 g. Each animal received only one injection and the number of animals ovulating was counted. For comparison, a group of rats were also injected with Gn—RH and the results are given in parentheses in the table below:

TABLE

| Dose/Rat μg. | No. of animals | Number ovulating | (Gn-RH) |
| --- | --- | --- | --- |
| 0 | 6 | 1 | 6 - 1 |
| 0.004 | 6 | 1 | 5 - 1 |
| 0.012 | 5 | 1 | |
| 0.02 | 5 | 4 | 7 - 1 |
| 0.1 | 4 | 4 | 5 - 5 |
| 0.5 | 2 | 2 | 2 - 2 |

While the above table shows that the compound of structure I shows ovulatory effect at a much lower dose than the same effect with Gn-RH, the even more surprising fact is that ovulation can be induced in rats at a dose of 0.003 mg./kg. upon oral administration while Gn—RH requires 62—250 μg./kg. orally to produce the same results.

Since the above compounds are easily soluble in physiological saline, the preparation of injectable solutions is simple and solutions containing 1—10% of the above compound can easily be prepared. If desired, a preservative such as benzyl alcohol is added to improve storage stability of solutions that are not intended to be used promptly, although this is not necessary since the peptide chain does not decompose rapidly.

For oral preparations, any number of pharmaceutical forms can be used, e.g., syrups, elixirs, suspensions or the compound can be processed into wafers, pills, tablets and the like. However, since the dosage producing ovulatory effects is extremely small, the usual tableting methods require the use of fillers and other excipients to prepare tablets of manageable size. In a preferred embodiment, the oral dosage form consists of a tablet containing between 0.1 and 5.0 mg. of the above peptide per tablet. Such tablets can be coated in the usual fashion, preferably using a readily soluble coating material, e.g., sugar, etc. or the above amount can be incorporated into gelatin capsules which promptly dissolve upon introduction into the stomach. In any event, the usual flavoring and coloring agents can be used without effect on the active peptide so incorporated.

In practice and as well known by those skilled in the art of animal husbandry, ovulation can obviously be induced only in animals that have a suitably mature ovarian follicle. Thus, a female in the reproductive age can be given the above dose of the compound of formula I in repeated administrations until ovulation occurs. Once this has been accomplished, no further ovulation can be induced until a mature follicle has been formed again at which time the administration of the new compounds will have the desired effect again.

What is claimed is:

1. A nonapeptide of the formula:

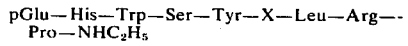

wherein all aminoacids are present in their optical L-configuration and wherein X represents leucyl in the D-configuration.

* * * * *